United States Patent [19]

Gokhberg et al.

[11] 4,147,736
[45] Apr. 3, 1979

[54] METHOD OF PREPARING ISOPRENE AND ISOAMYLENES

[76] Inventors: Pavel Y. Gokhberg, prospekt Stoletova, 50, kv. 127, Volgograd; Boris N. Gorbunov, ulitsa Stepana Razina, 11/13, kv. 9, Tambov; Alexandr P. Khardin, ulitsa Krasnopiterskaya, 2, kv. 32, Volgograd; Vladimir L. Rudkovsky, prospekt Lenina, 33, kv. 6; Valentin M. Belyaev, prospekt Lenina, 32, kv. 20, both of Volzhsky Volgogradskoi oblasti; Anatoly I. Lukashov, ulitsa Palekhskaya, 9, korpus 1, kv. 65, Moscow; Ljudmila V. Shpantseva, ulitsa Karbysheva, 54; Vitaly V. Orlyansky, ulitsa Sovetskaya, 5, kv. 21, both of Volzhsky Volgogradskoi oblasti, all of U.S.S.R.

[21] Appl. No.: 796,067

[22] Filed: May 12, 1977

[51] Int. Cl.² ............................................. C07C 1/20
[52] U.S. Cl. ............................. 260/681; 260/677 R; 260/682
[58] Field of Search .................. 260/681, 682, 677 R

[56] References Cited

U.S. PATENT DOCUMENTS

| | | | |
|---|---|---|---|
| 3,621,072 | 11/1971 | Watanabe et al. | 260/681 |
| 3,845,155 | 10/1974 | Heckelsberg | 260/681 |

*Primary Examiner*—C. Davis
*Attorney, Agent, or Firm*—Lackenbach, Lilling & Siegel

[57] ABSTRACT

The method of preparing isoprene and isoamylenes consists in that a gaseous mixture of isobutylene and methyl alcohol is brought in contact with a catalyst, namely aluminum oxide or tantalum pentoxide, at a temperature of 250 to 500° C. It is recommendable that use should be made of aluminum oxide modified with an oxide of at least one of the following elements: molybdenum, tungsten, chromium, zirconium, titanium, vanadium, and cobalt. Moreover, it is possible to use aluminum oxide modified with a sulphate of at least one of the following elements: zirconium and chromium. A combination of both modifications is also possible. The yield of isoprene obtained by the proposed method is 16 to 20 mol. percent, with respect to the passed methyl alcohol, and the yield of isoamylenes is 25 to 30 mol. percent.

5 Claims, No Drawings

METHOD OF PREPARING ISOPRENE AND ISOAMYLENES

This invention relates to methods of preparing isoprene and isoamylenes.

Said isoprene and isoamylenes are widely used in chemical industry, e.g. in the manufacture of polyisoprene rubber and high-quality petrols.

Known in the prior art is an industrial method for preparing isoprene, comprising the following main three steps: oxidation of methyl alcohol to formaldehyde, condensation of formaldehyde with isobutylene, and splitting of 4,4-dimethyldioxane-1,3 to isoprene.

The disadvantage of the known method is that the process is realized in a plurality of steps, and, as a result, a great number of side products are produced alongside with the main product.

Known in the prior art is a method for preparing isoprene and isoamylenes utilizing the same starting reagents (isobutylene and methyl alcohol). The end products are obtained by this method in one stage only, as a result of bringing a mixture of isobutylene, methyl alcohol (and/or dimethyl ether) and oxygen in contact with a solid catalyst at a temperature of 100° to 500° C. The catalyst used according to this method are oxides of at least one of the following elements: melybdenum, tungsten, uranium, vanadium, phosphorus, and others. The catalysts can be used per se or applied onto a silica gel carrier.

The method is characterized by a relatively low yield of isoprene (to 22 mol.% with respect to the passed methyl alcohol), insignificant yield of isoamylene (tenth fractions of percent), and low productivity of the catalyst.

It is an object of the present invention to provide a method of preparing isoprene and isoamylenes, that would ensure high yields of the end products.

In accordance with this and other objects, the invention consists in that a gaseous mixture of isobutylene and methyl alcohol is brought in contact with a catalyst, namely aluminum oxide or tantalum pentoxide, at a temperature of 250° to 500° C.

It is recommendable to use aluminum oxide modified with an oxide of at least one of the following elements: molybdenum, tungsten, chromium, zirconium, titanium, vanadium, cobalt.

Moreover, it is recommendable also to use aluminum oxide modified with a sulphate of at least one of the following elements: zirconium or chromium.

It is also possible to use aluminum oxide modified with oxides and sulphates of the above cited elements.

As a result of the absence of oxygen and of utilization of said catalyst, the yield of isoprene in the proposed method is 16 to 20 mol% with respect to the passed methyl alcohol and the yield of isoamylenes is 25 to 30 mol. percent. Isoamylenes are valuable intermediates in the manufacture of isoprene (they are readily dehydrogenated into isoprene), in the manufacture of high-quality petrols, etc.

Aluminum oxide that is used as a catalyst according to the herein-proposed method is an active form of alumina containing mainly $\gamma$-$Al_2O_3$.

If a modified aluminum oxide is used as the catalyst, the latter is prepared as follows:

(a) by the reaction of aluminum oxide with oxides and/or sulphates of the above-said elements, in the solid phase; or (b) by impregnating aluminum oxide with aqueous solutions of salts of at least one of the above-said elements, with subsequent calcining at a temperature of 450° to 600° C.

The choice of the calcining temperature in carrying out the herein-proposed method depends on the particular type of the catalyst used. In order to attain higher yields of the end products, it is recommended that the molar ratio of isobutylene to methyl alcohol, as they contact the catalyst, should be from 1:1 to 20:1.

The herein-proposed method can be realized by delivering either a 100 percent methyl alcohol or its aqueous solutions into the reaction vessel. If aqueous solutions of methyl alcohol are used, the reaction of isobutylene with methyl alcohol should be effected in the atmosphere of steam which decreases the quantity of coke deposited on the catalyst.

For a better understanding of the invention, the following examples of its practical embodiment are given by way of illustration. (The yields of the end products are given in a Table that follows the Examples).

EXAMPLE 1

An active aluminum oxide calcined at a temperature of 400° C. and crushed to 0.4 to 0.8 mm particles, is used as the catalyst. 20 ml of thus prepared catalyst are placed in a silica reactor provided with a side arm for thermocouples. The inner diameter of the reactor is 28 mm and the outer diameter of the side arm is 13 mm. The experiment is carried out by passing the reagents through a stationary bed of the catalyst in said silica reactor. The temperature of the catalyst is 400° C. The system is blown with nitrogen to ensure the neutral medium of the reaction. The nitrogen stream is then discontinued and isobutylene and methyl alcohol, taken in the molar ratio of 2.3:1, are passed into the reactor.

Methyl alcohol is injected by a laboratory batcher, at a rate of 8.6 ml per hour, into the stream of isobutylene, directly before the entrance into the reactor. The pressure inside the system is practically atmospheric. The content of unsaturated iso-$C_5$ hydrocarbons in the contact gas is determined by gas chromatography.

EXAMPLE 2

An active tantalum pentoxide, pressed into tablets, calcined at a temperature of 400° C. and crushed to 0.4 to 0.8 mm particles, is used as the catalyst. 20 ml of the thus prepared catalyst are placed into a silica reactor. The conditions of the experiment are the same as described in Example 1, except that the reaction temperature in the catalyst bed is 450° C.

EXAMPLE 3

The catalyst used in this experiment is prepared as follows. 15.5 g of active aluminum oxide are crushed to 0.4 to 0.8 mm particles, impregnated in 10.44 g of an aqueous solution containing 15.4 percent by weight of chromium sulphate and 20.6 percent by weight of zirconium sulphate, and the solution is evaporated. The catalyst is dried at a temperature of 80° C. and calcined for three hours at a temperature of 450° C. 20 ml of the obtained catalyst are used in the reaction. The conditions of the reaction are the same as in Example 1, except that the temperature is 450° C.

EXAMPLE 4

Four catalyst samples are prepared as follows. Active aluminum oxide is crushed to 0.4–0.8 mm particles and impregnated with an aqueous solution of ammonium molybdate $(NH_4)_6Mo_7O_{24}\cdot 4H_2O$. The solution is evaporated, the samples are dried at a temperature of 120° C. and calcined at a temperature of 450° C. for four hours. The molar ratios of $MoO_3$ to $Al_2O_3$ in the thus obtained catalysts are:

(a) 0.05, (b) 0.10, (c) 0.15, and (d) 0.20. Each catalyst is used in the reaction in the quantity of 20 ml. The conditions of the experiments with each type of the catalyst are the same as described in Example 1, except that the molar ratio of isobutylene to methyl alcohols is 7.9:1.

EXAMPLE 5

The catalyst is prepared as follows. 21.8 g of active aluminum oxide crushed to 0.4 to 0.8 mm particles are impregnated with an aqueous solution containing 7.55 g of ammonium molybdate $(NH_4)_6Mo_7O_{24}\cdot 4H_2O$, the solution is evaporated, the catalyst is dried at a temperature of 120° C, and calcined for four hours at a temperature of 450° C.

20 ml of the thus prepared catalyst are used in the experiment. The reaction conditions are the same as described in Example 4, except that the space velocity of the water-methanol solution (methanol to water ratio 1:1) delivered into the reactor is 0.43 hour$^{-1}$ (as calculated for methyl alcohol).

EXAMPLE 6

The catalyst is prepared as follows. 15.57 g of active aluminum oxide are impregnated with a solution of 1.91 g of tungstic acid in ammonia, the solution is evaporated, and the catalyst dried for four hours at a temperature of 450° C. 20 ml of the thus prepared catalyst are used in the experiment (grain size 0.4 to 0.8 mm). The reaction conditions are the same as in Example 4.

EXAMPLE 7

The catalyst used in the experiment is prepared as follows. 23.83 g of active aluminum oxide are crushed to 0.4 to 0.8 mm particles, and impregnated with a solution of 1.37 g of ammonium metavanadate in water. The solution is evaporated to dryness, and the catalyst is then dried at a temperature of 90° C. with subsequent calcining for four hours at a temperature of 450° C. 20 ml of the thus prepared catalyst are loaded into the reactor. The reaction conditions are the same as in Example 4.

EXAMPLE 8

The catalyst used in the experiment is prepared as follows. 22.04 g of active aluminum oxide are crushed to 0.4 to 0.8 mm particles and impregnated with an aqueous solution containing 4.32 g of chromium nitrate $Cr(NO_3)_3\cdot 6H_2O$. The solution is evaporated at a temperature of 90° C. and calcined for four hours at a temperature of 450° C. 20 ml of the thus prepared catalyst are used in the reaction, the conditions of which are the same as described in Example 4.

EXAMPLE 9

The catalyst used in the experiment is prepared as follows. 34.1 g of active aluminum oxide are crushed to 0.4 to 0.8 mm particles and impregnated with a solution containing 5.93 g of zirconium sulphate, $Zr(SO_4)_2\cdot 4H_2O$. The aqueous solution is then evaporated and calcined for four hours at a temperature of 450° C. 20 ml of the thus prepared catalyst are used in the reaction. The conditions of the experiment are the same as described in Example 4.

EXAMPLE 10

The catalyst used in the experiment is prepared as follows. 20 g of active aluminum oxide are crushed to powder, and mixed thoroughly with 0.78 g of titanium dioxide. The mixture is pressed into tablets and calcined for four hours at a temperature of 450° C. The tablets are then crushed to 0.4 to 0.8 mm particles. 20 ml of the thus prepared catalyst are used in the reaction. The reaction conditions are the same as in Example 4.

EXAMPLE 11

The catalyst used in the experiment is prepared as described in Example 3. The prepared catalyst is taken in the quantity of 20 ml, and the reaction temperature is raised to 500° C. The molar ratio of isobutylene to methanol is 2.3:1. The rate of methanol delivery is 8.6 ml per hour.

EXAMPLE 12

The catalyst used in the experiment is prepared as follows. 50 g of active aluminum oxide, having granules sizing from 0.4 to 0.8 mm, are impregnated with an aqueous solution containing 12.98 g of ammonium molybdate, $(NH_4)_6Mo_7O_{24}\cdot 4H_2O$, then dried at a temperature of 100° C., and calcined at a temperature of 450° C. for four hours.

The reaction conditions are the same as in Example 4, except that the reaction temperature is 250° C.

EXAMPLE 13

31.5 g of active aluminum oxide, having particles sizing from 0.4 to 0.8 mm, are impregnated with an aqueous solution containing 4.49 g of cobalt nitrate. The solution is evaporated, the catalyst is dried at a temperature of 100° C. and then calcined at a temperature of 450° C. for four hours. The reaction conditions are the same as in Example 4.

EXAMPLE 14

The catalyst used in the experiment is prepared as follows. Active aluminum oxide is impregnated in an aqueous solution of ammonium molybdate, the solution is evaporated, the solid phase dried, impregnated with an aqueous solution of zirconium sulphate, and then dried at a temperature of 100° C. with subsequent calcining at a temperature of 450° C. for four hours. The obtained catalyst has the composition of $MoO_3$-$Zr(SO_4)_2$-$Al_2O_3$; the molar ratio of $MoO_3$ to $Al_2O_3$ is 0.10, and of $Zr(SO_4)_2$ to $Al_2O_3$ is 0.05. The reaction conditions are the same as in Example 4.

EXAMPLE 15

The catalyst used in the experiment is prepared as follows. Active aluminum oxide is impregnated with an aqueous solution containing ammonium molybdate and ammonium vanadate. The solution is evaporated and the catalyst dried at a temperature of 110° C. with subsequent calcining at a temperature of 600° C. for four hours. The obtained catalyst has the composition of $MoO_3$—$V_2O_5$—$Al_2O_3$; the molar ratio of $MoO_3$ to $Al_2O_3$ is 0.10 and of $V_2O_5$ to $Al_2O_3$ is 0.025. The reaction conditions are the same as in Example 4.

The Table that follows below gives the yields of the end products obtained according to the proposed invention, as described in Examples 1 through 15 (the yield is given with respect to the passed methanol and expressed in mol. percent).

Table

| Ex. No. | Iso-prene | 2-methyl-butene-1 | 2-methylbutene-2 | 3-methylbutene-1 |
|---|---|---|---|---|
| 1 | 2.73 | 4.04 | 8.93 | 1.18 |
| 2 | 6.53 | 2.34 | 5.5 | traces |
| 3 | 4.26 | 4.91 | 11.41 | 1.68 |
| 4a | 7.38 | 7.8 | 19.91 | 2.32 |
| 4b | 10.46 | 8.45 | 23.26 | 3.14 |
| 4c | 14.97 | 6.28 | 20.32 | 4.26 |
| 4d | 15.99 | 6.53 | 15.25 | 4.27 |
| 5 | 9.96 | 10.05 | 24.49 | 4.64 |
| 6 | 1.33 | 8.63 | 20.46 | 1.03 |
| 7 | 17.3 | 2.7 | 7.0 | 2.36 |
| 8 | 7.87 | 1.14 | 2.62 | 1.00 |
| 9 | 4.2 | 9.2 | 24.3 | 1.45 |
| 10 | 9.17 | 7.2 | 13.18 | 2.13 |
| 11 | 2.86 | 5.27 | 10.93 | 1.28 |
| 12 | 2.32 | 0.33 | 1.33 | traces |
| 13 | 4.52 | 1.17 | 2.43 | traces |
| 14 | 10.27 | 3.10 | 7.11 | 1.06 |
| 15 | 5.01 | 9.05 | 19.60 | 3.11 |

What is claimed is:

1. A method for preparing isoprene and isoamylenes, comprising contacting a metal oxide catalyst selected from the group consisting of:
   (i) aluminum oxide modified with an oxide of at least one of the elements selected from the group consisting of molybdenum, tungsten, chromium, titanium, vanadium, and cobalt, or
   (ii) aluminum oxide modified with chromium sulfate, or
   (iii) tantalum pentoxide,
   with a gaseous mixture of isobutylene and methyl alcohol, having a molar ratio of 1:1 to 20:1, respectively, at a temperature of 250° to 500° C., in the absence of oxygen.

2. A method according to claim 1, wherein said catalyst consists of aluminum oxide modified with an oxide of at least one of the elements selected from the group consisting of molybdenum, tungsten, chromium, titanium, vanadium, and cobalt.

3. A method according to claim 1, wherein said catalyst consists of aluminum oxide modified with chromium sulphate.

4. A method according to claim 1, wherein said catalyst consists of aluminum oxide modified with
   (a) an oxide of at least one of the elements selected from the group consisting of molybdenum, tungsten, chromium, titanium, vanadium, cobalt; and
   (b) chromium sulphate.

5. A method according to claim 1, wherein said metal oxide catalyst is tantalum pentoxide.

* * * * *